(12) United States Patent
Schneider et al.

(10) Patent No.: US 11,925,375 B2
(45) Date of Patent: Mar. 12, 2024

(54) MEDICAL INSTRUMENT AND METHOD

(71) Applicant: KARL STORZ SE & Co. KG, Tuttlingen (DE)

(72) Inventors: Janosz Schneider, Tuttlingen (DE); Jochen Stefan, Tuttlingen (DE); Daniel Kärcher, Tuttlingen (DE); Robin Merz, Tuttlingen (DE); Sven Axel Grüner, Tuttlingen (DE); Martin Blocher, Tuttlingen (DE); Sven Schneider, Tuttlingen (DE); Tobias Unger, Tuttlingen (DE); Dominik Längle, Tuttlingen (DE); Judith Holzer, Tuttlingen (DE); Sebastian Wagner, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 18/014,800

(22) PCT Filed: Jul. 5, 2021

(86) PCT No.: PCT/EP2021/068525
§ 371 (c)(1),
(2) Date: Jan. 6, 2023

(87) PCT Pub. No.: WO2022/008453
PCT Pub. Date: Jan. 13, 2022

(65) Prior Publication Data
US 2023/0210548 A1 Jul. 6, 2023

(30) Foreign Application Priority Data
Jul. 8, 2020 (DE) .......................... 102020117962.6

(51) Int. Cl.
*A61B 17/29* (2006.01)
*A61B 17/00* (2006.01)
(52) U.S. Cl.
CPC .. *A61B 17/2909* (2013.01); *A61B 2017/0046* (2013.01); *A61B 2017/00862* (2013.01);
(Continued)

(58) Field of Classification Search
CPC ........ A61B 17/2909; A61B 2017/0046; A61B 2017/00862; A61B 2017/292; A61B 2017/2946
See application file for complete search history.

(56) References Cited

U.S. PATENT DOCUMENTS 5,174,300 A 12/1992 Bales et al.
5,588,581 A 12/1996 Conlon et al.
(Continued)

FOREIGN PATENT DOCUMENTS

DE 9213119 U1 11/1992
EP 2564794 A1 3/2013

OTHER PUBLICATIONS

Oct. 21, 2021—(WO) International Search Report & Written Opinion—App. No. PCT/EP2021/068525.
(Continued)

*Primary Examiner* — Brooke Labranche
(74) *Attorney, Agent, or Firm* — Banner & Witcoff, Ltd.

(57) ABSTRACT

The invention relates to a medical instrument having an elongated shaft, a movable tool at a distal end of the shaft, a handle with a movable grip part at a proximal end of the shaft, and a force transmission element which can be moved in the longitudinal direction of the instrument and is operatively connected to the movable grip part and to the tool such that an actuation of the movable grip part is converted into a movement of the tool. The instrument has a spring assembly that is arranged on the handle and has at least one leg spring, which has at least one winding and two legs, and a pin, wherein the at least one winding extends about the pin. When the movable grip part is actuated, a force is applied to at least one of the legs of the leg spring, said force reducing the friction between the winding and the pin such that the leg spring can be rotated about the pin and the force transmission element and the tool can be moved. When a force is transmitted from the tool to the force transmission element in the longitudinal direction thereof, the leg spring cannot be rotated about the pin such that the force transmission element and the tool cannot be moved.

18 Claims, 5 Drawing Sheets

Figure 1:
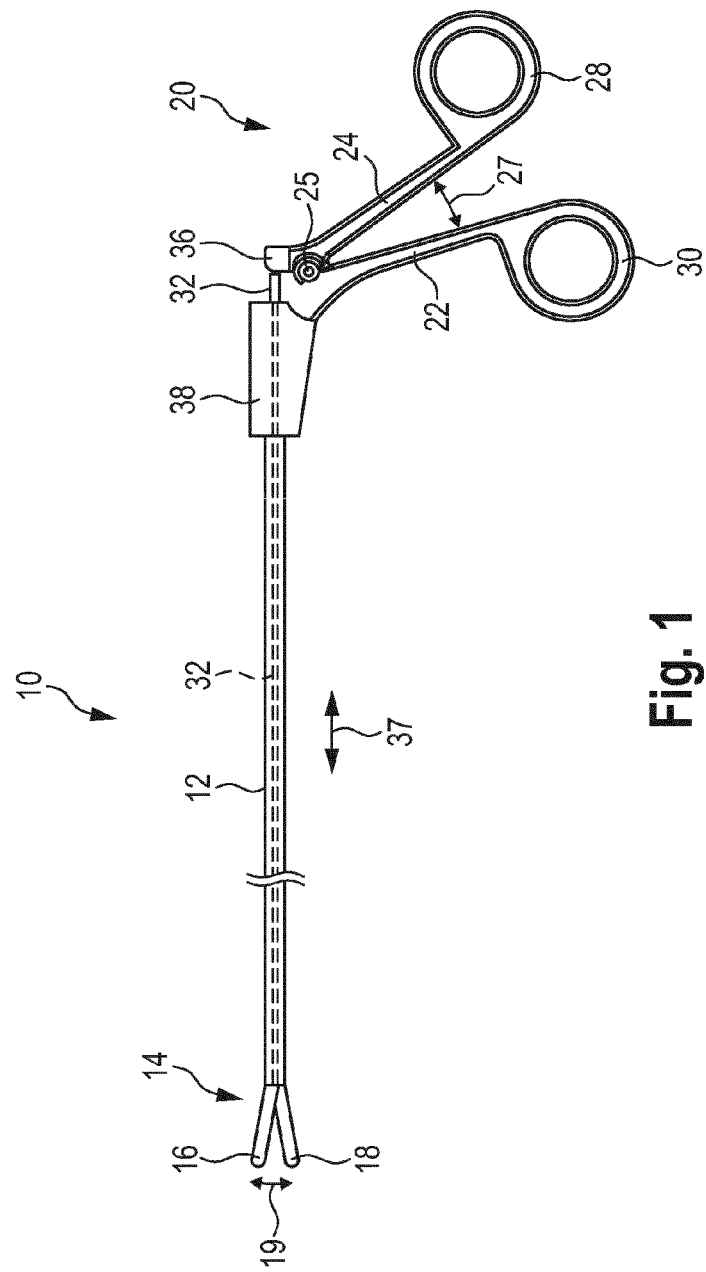

(52) U.S. Cl.
CPC . *A61B 2017/2912* (2013.01); *A61B 2017/292* (2013.01); *A61B 2017/2946* (2013.01)

(56) References Cited

U.S. PATENT DOCUMENTS

| | | |
|---|---|---|
| 2004/0167569 A1 | 8/2004 | Dicesare et al. |
| 2008/0083813 A1* | 4/2008 | Zemlok ................ A61B 17/068 227/181.1 |
| 2009/0177039 A1 | 7/2009 | Frank |

OTHER PUBLICATIONS

May 3, 2021—(DE) Examination Report—App. No. 10 2020 117 962.6.
Apr. 19, 2022—(DE) Decision to Grant—App. No. 10 2020 117 962.6.

* cited by examiner

MEDICAL INSTRUMENT AND METHOD

CROSS-REFERENCE TO RELATED APPLICATIONS

The present application claims priority from and is a U.S. National Phase of International Application No. PCT/EP2021/068525, which was filed on Jul. 5, 2021, designating the United States of America and claiming priority to German Patent Application No. DE 10 2020 117 962.6, filed on Jul. 8, 2020. This application claims priority to and the benefit of the above-identified applications, which are all fully incorporated by reference herein in their entireties.

The invention relates to a medical instrument having an elongated shaft, a movable tool at a distal end of the shaft, a handle with a movable grip part at a proximal end of the shaft, and a force transmission element which can be moved in the longitudinal direction of the instrument and is operatively connected to the movable grip part and to the tool such that an actuation of the movable grip part is converted into a movement of the tool.

The invention further relates to a method for immobilizing and enabling the movability of a movable tool of a medical instrument.

Medical instruments, which are designed for example as surgical cutting and grasping forceps, are known from the company brochure STORZ-THE WORLD OF ENDOSCOPY, Volume LAPAROSCOPY IN SURGERY, GYNECOLOGY, UROLOGY 8th Edition 2/2016/US. A surgical forceps has an elongated shaft, a tool with one or a plurality of jaw parts for cutting or grasping at the distal end of the shaft and a handle with a movable grip part at the proximal end of the shaft. By means of a force transmission element, which extends in the longitudinal direction of the shaft, an actuation of the movable grip part is converted into a movement of one or of the plurality of jaw parts, for example to open or close the tool of the instrument.

For example in the case of grasping forceps with jaw parts, of which at least one is movable, when the surgeon has closed the jaw parts by means of actuating the movable grip part to such an extent that the object to be grasped is securely grasped, it is often desirable for them to be able to release the movable grip part or at least reduce the hand force without the jaw parts reopening to such an extent that the grasped object falls from the tool.

For this purpose, in the case of the known instruments, a snap-in locking mechanism is arranged on the handle between the grip parts, said snap-in locking mechanism having a number of snap-in locking teeth, which make it possible for the movable grip part to be immobilized in the opening direction of the tool. By immobilizing the movable grip part, the longitudinal movement of the force transmission element in the direction of movement, which corresponds to the opening of the tool, is locked and the tool cannot open in an undesired manner.

A snap-in locking mechanism for immobilizing the tool of the instrument has, however, the disadvantage that a snap-in lock is only possible at predefined distances, which are predefined by the distance of adjacent teeth. This can for example lead to the surgeon having to move the movable grip part further than required in order to securely grasp the object in order to reach the next snap-in locking point. This can, in turn, lead to the object to be grasped, for example a surgical needle, being grasped with excessive force by the jaw parts and may be damaged as a result. Additionally, an excessive tension may occur in the force transmission element, which may lead to the force transmission element being damaged. Locking of the movable grip part under high tension of the force transmission element can lead to the force transmission element tearing.

A medical instrument is known from EP 2 564 794 A1, whose shaft is rotatable about its longitudinal axis relative to the handle. In the case of this instrument, a spring assembly is present that has a leg spring, which is wrapped around a gripping element in order to hold the shaft and the handle relative to one another in a rotationally-fixed manner, wherein a rotary movement is, however, possible when an actuating element is actuated to rotate the shaft.

The patent application US 2009/0177039 A1 also discloses a medical instrument having a shaft that is rotatable about its longitudinal axis. To rotate the shaft, an actuating element is attached to the handle. A friction element at the proximal end of the shaft prevents its rotation, unless a torque is applied from the actuating element.

The U.S. Pat. No. 5,588,581 A teaches the use of a leg spring in a handle in order to return its compressible grip parts to their spread-out starting position.

The object underlying the invention is to provide a medical instrument of the type mentioned at the outset with continuous immobilization of the movability of the tool.

The object further underlying the invention is to indicate a method for immobilizing and enabling the movability of a movable tool of a medical instrument.

According to the invention, the first-mentioned object is achieved by a medical instrument, having an elongated shaft, a movable tool at a distal end of the shaft, a handle with a movable grip part at a proximal end of the shaft, and a force transmission element which can be moved in the longitudinal direction of the instrument and is operatively connected to the movable grip part and to the tool such that an actuation of the movable grip part is converted into a movement of the tool, and having a spring assembly that is arranged on the handle and has at least one leg spring, which has at least one winding and two legs, and a pin, wherein the at least one winding extends about the pin, wherein when the movable grip part is actuated, a force is applied to at least one of the legs of the leg spring, said force reducing the friction between the winding and the pin such that the leg spring can be rotated about the pin and the force transmission element and the tool can be moved, whereas when a force is transmitted from the tool to the force transmission element in the longitudinal direction thereof, the leg spring cannot be rotated about the pin such that the force transmission element and the tool cannot be moved.

In the case of the medical instrument according to the invention, a continuous self-locking is implemented for the tool, which instantaneously counteracts any force application on the force transmission element coming from the tool and prevents a movement of the tool when a movement of the tool is not actuated in a desired manner by actuating the movable grip part. If the tool is for example configured as a grasping tool and if an object is grasped with the tool, the object exerts a force on the tool in the opening direction of the tool. This force exerted by the object is transmitted to the force transmission element, which would be moved in the longitudinal direction without the self-locking provided according to the invention when the surgeon releases the movable grip part. In the case of the instrument according to the invention however, when the grip part is released, self-locking of the movement of the tool takes effect immediately due to the frictional engagement between the at least one winding of the leg spring and the pin. The force transmitted from the tool to the force transmission element may even increase the friction between the at least one winding of the leg spring and the pin by the winding being wrapped even more tightly around the pin. The self-locking occurs automatically in any position of the tool when the movable grip part is not actuated in order to intentionally move the tool. The self-locking of the instrument according to the invention is preferably continuous over the entire possible movement path of the tool. If the movable grip part is actuated, the friction between the at least one winding of the leg spring and the pin is, in contrast, reduced such that the leg spring can rotate about the pin. A reduction of the friction may also include complete removal of any friction. The self-locking mechanism of the instrument according to the invention is therefore not only continuous, but rather also has the further advantage that a release mechanism to be operated separately is not required for releasing the self-locking, which simplifies the operation of the medical instrument and also keeps the structural complexity of the self-locking mechanism low.

The configuration of the medical instrument according to the invention is advantageous not only for grasping forceps or grasping instruments, but also for cutting forceps or cutting instruments. In the case of a cutting instrument, the tool is designed as a cutting tool and has for example two jaw parts acting with one another in a cutting manner. The self-locking mechanism according to the invention can for example prevent an undesired closure of the tool, i.e. closure of the tool can only be effected by actuating the movable grip part.

The at least one winding of the leg spring can preferably already be wrapped tightly around the pin in the rest state to such an extent that the leg spring cannot be rotated about the pin in the rest state due to friction.

The advantage here is that the self-locking is effective even with the smallest forces transmitted from the tool to the force transmission element, whereby self-locking is always ensured.

The self-locking mechanism can also be designed such that a force transmitted from the tool to the force transmission element in its longitudinal direction is applied to at least one of the legs, whereby the friction between the at least one winding and the pin is increased.

In this configuration, a force transmitted from the tool to the force transmission element acts on the leg or legs of the leg spring in a manner that increases friction by the winding being wrapped even more tightly around the pin.

Essentially, it can be provided that the self-locking acts either only in the closing direction of the tool or only in the opening direction of the tool. The self-locking can, however, preferably be effective both in the opening and in the closing direction of the tool.

Thus, it can be provided that the longitudinal movement of the force transmission element and the movement of the tool is locked both when the force acting via the tool on the force transmission element is directed distally and when the force acting via the tool on the force transmission element is directed proximally.

In other words, the self-locking is always effective, regardless of whether the force transmitted from the tool attempts to pull the force transmission element distally or push it proximally.

Similarly, the free mobility of the longitudinal movement of the force transmission element can be free in the distal direction and proximal direction when the movable grip part is moved in its two actuating directions. To this end, it is preferably provided that in the two actuating directions of the movable grip part, a force is applied to each one of the legs of the leg spring, said force reducing the friction between the winding and the pin.

The self-locking and the free mobility of the tool movement can therefore be effective bidirectionally in each case.

When the movable grip part is pivotable about an axis of rotation, as is provided in one configuration, the pin preferably aligns with the axis of rotation.

On the one hand, a space-saving arrangement of the spring assembly is hereby implemented. On the other hand, favorable lever ratios result in order to exert a force on the leg or legs by actuating the movable grip part, said force reducing the friction between the at least one winding of the leg spring and the pin.

In one constructively simple configuration, the movable grip part has a driver, which exerts the force on at least one of the legs of the leg spring when the movable grip part is actuated in order to reduce the friction between the winding and the pin. The driver can for example move one leg relative to the other leg such that the diameter of the winding is enlarged and the friction with the pin reduced as a result.

The legs of the leg spring preferably project from the at least one winding towards the same side and the driver is arranged between the legs of the leg spring.

When the movable grip part moves in one actuating direction, the driver can act on a first of the two legs of the leg spring and move it away from the second end of the leg spring, whereby the friction between the spring winding and the pin is for example reduced. If the movable grip part is actuated in the opposing direction of movement, the driver can move the second end of the leg spring away from the first end of the leg spring, whereby the friction between the spring winding and the pin is, in turn, for example reduced. The legs can be arranged axially behind one another viewed in the longitudinal direction of the shaft, while the driver extends transversely to the longitudinal direction of the shaft in a plane, which contains the longitudinal axis of the shaft.

The movable grip part can have a receiving portion for connecting a proximal end of the force transmission element to the movable grip part, and at least one leg, preferably both legs, can be fixedly connected, directly or indirectly, to the receiving portion.

When a force acts from the tool on the force transmission element and attempts to move the force transmission element in the distal or proximal direction, this force is transmitted from the receiving portion to the legs of the leg spring without the friction of the spring winding with the pin being reduced and therefore the self-locking being effective. Such a force can, however, wrap the winding of the leg spring more tightly around the pin and therefore increase the friction between the winding and the pin.

The spring assembly can have at least two leg springs, which are preferably arranged on both sides of a longitudinal central axis of the shaft.

For reasons of space in the region of the grip, the eccentric arrangement of the spring assembly is advantageous. The two-sided arrangement of the spring assembly in relation to the longitudinal central axis has the advantage of an improved effect of the self-locking due to a friction increased by at least two spring windings as well as a symmetric load distribution of the self-locking mechanism. The pin can extend on both sides of the longitudinal central axis of the shaft, or a pin is in each case present on both sides of the longitudinal central axis.

The spring assembly can also have more than two leg springs, for example four leg springs, which are arranged in pairs on both sides of the longitudinal central axis of the shaft.

The self-locking effect of the spring assembly is improved with the number of leg springs because, due to the higher number of leg springs, the friction between the windings of the leg springs and the pin or pins is greater.

Alternatively or additionally, the at least one leg spring can have a plurality of windings. A greater friction between the leg spring and the pin can also be produced in this way.

Moreover, the spring assembly can have an anti-torsion mechanism which ensures that the leg spring(s) are stabilized against twisting.

Furthermore, a method for immobilizing and enabling the movability of a movable tool of a medical instrument is provided, which has an elongated shaft, the movable tool at a distal end of the shaft, a handle with a movable grip part at a proximal end of the shaft and a force transmission element which can be moved in the longitudinal direction of the instrument and which is operatively connected to the movable grip part and to the tool, wherein the movability of the tool and of the movable grip part is immediately prevented when the movable grip part is not actuated, and wherein the movability of the tool is immediately enabled by actuating the movable grip part.

The method has the same advantages as the instrument according to the invention.

Further advantages and features emerge from the following description and the enclosed drawing.

It is understood that the features mentioned above and still to be explained below can be used not only in the respectively indicated combination, but also in other combinations or alone without departing from the scope of the present invention.

Figure 2:
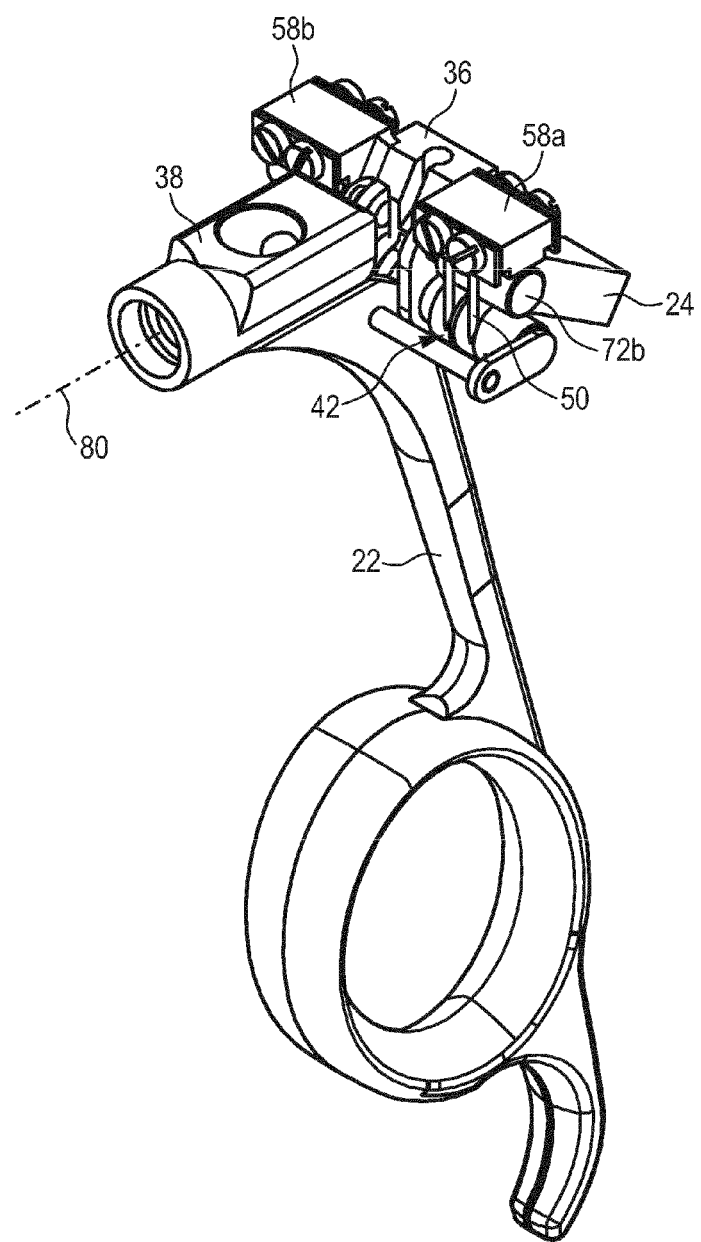
Figure 3:
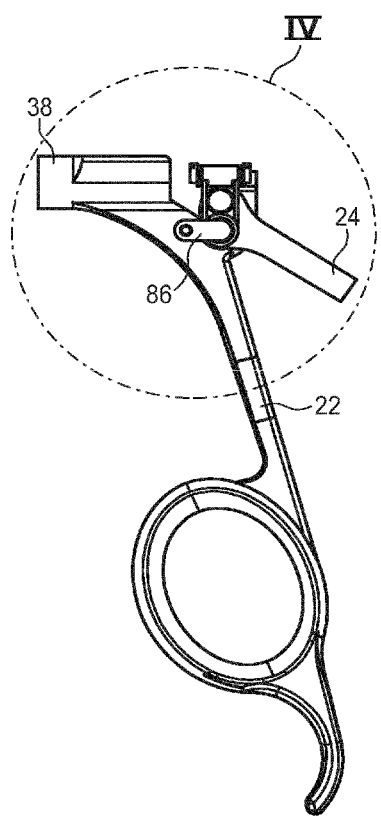
Figure 5:
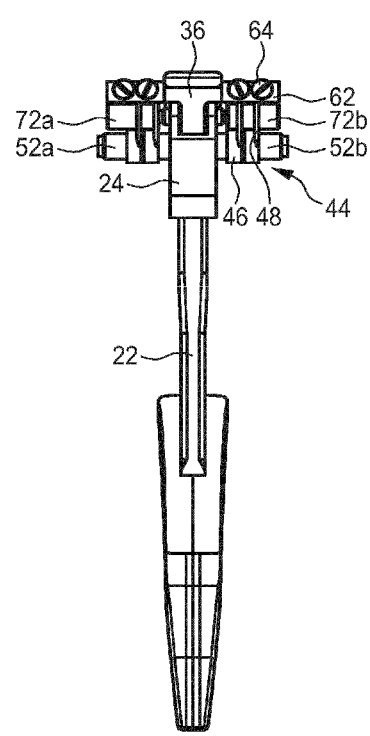
Figure 4:
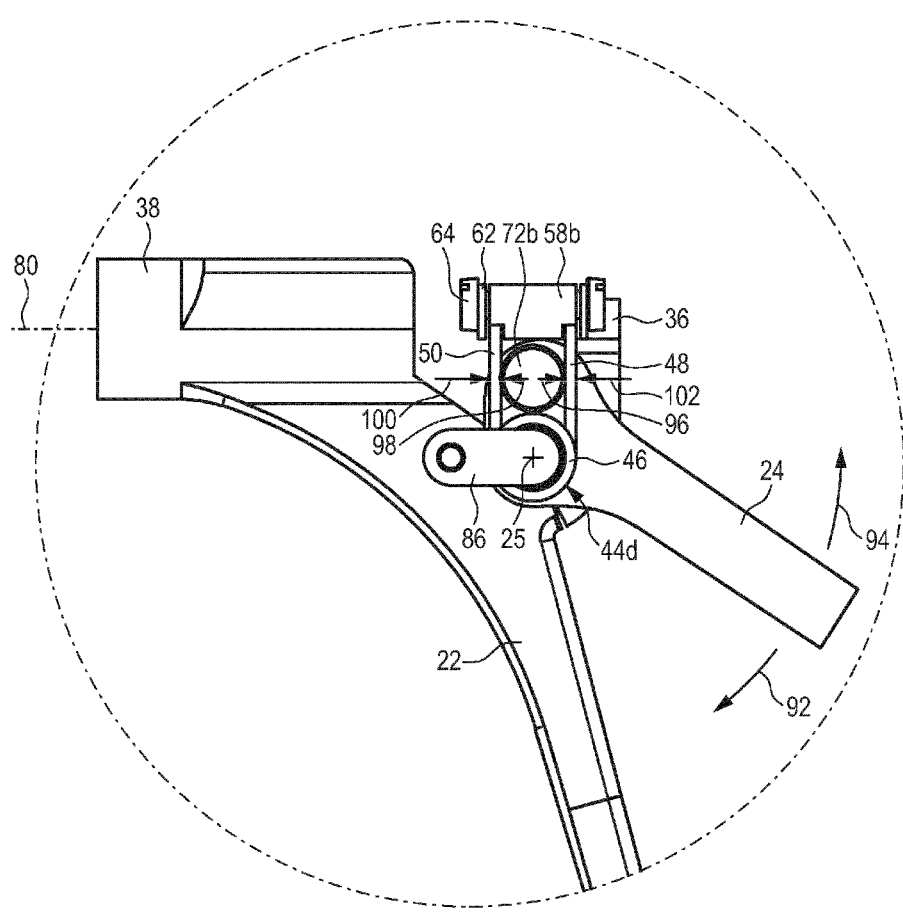

Exemplary embodiments of the invention are represented in the drawing and are described in more detail with reference to them hereafter, in which is shown:

FIG. 1 a side view of a medical instrument in a main representation;

FIG. 2 a section of a handle with a self-locking mechanism, as can be implemented in an instrument in FIG. 1, in a perspective representation;

FIG. 3 a side view of the arrangement in FIG. 2;

FIG. 4 an enlarged section of the arrangement in FIG. 3;

FIG. 5 a view from proximal towards the arrangement in FIG. 2; and

Figure 6:
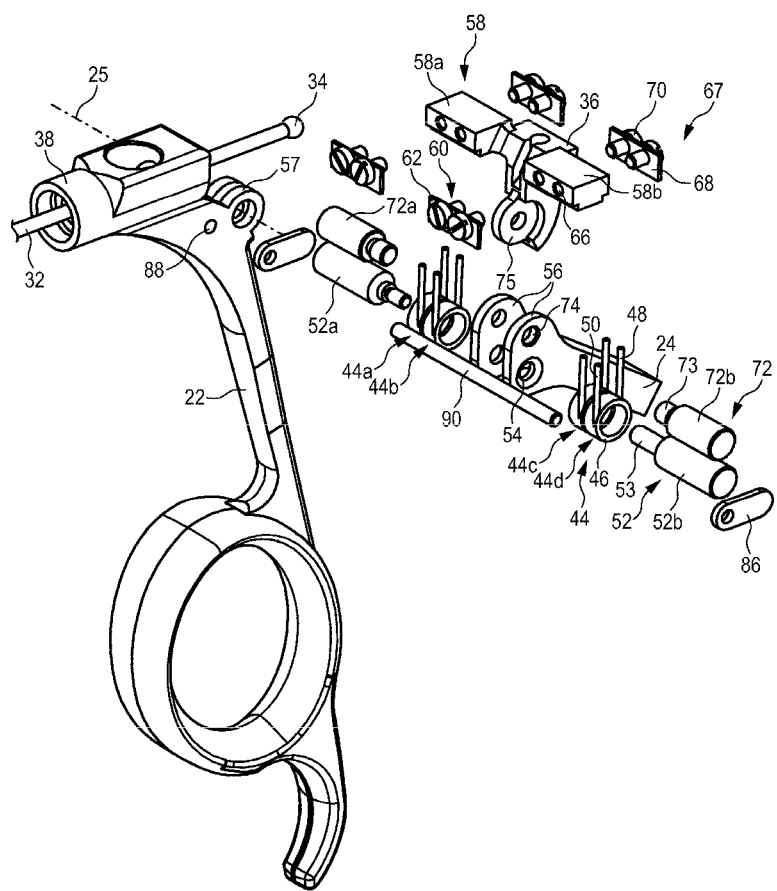

FIG. 6 an exploded drawing of the arrangement in FIG. 2 in perspective representation.

FIG. 1 shows a medical instrument provided with the general reference numeral 10. The medical instrument 10 can in particular be a surgical forceps.

The surgical forceps can be designed to cut, for example tissue, or to grasp tissue or other objects, such as for example a surgical needle, an implant or the like.

In general, the instrument 10 has an elongated shaft 12, on whose distal end is arranged a tool 14. The tool 14 can have a first jaw part 16 and a second jaw part 18. At least one of the two jaw parts 16, 18 is arranged on the distal end of the shaft so as to be movable, for example pivotable. The jaw parts 16 and 18 can, as illustrated with a double arrow 19, therefore be moved towards one another in order to close the tool 14, and they can be moved away from one another in order to open the tool 14.

The tool 14 can be designed in other configurations for example as a tool to hold back organs or tissue or as an applicator. The configuration of the tool 14 with jaw parts 16 and 18 is therefore only exemplary. A movement of the tool 14 can also consist of a translatory movement of the tool 14.

A handle 20 is arranged at the proximal end of the shaft 12. The handle 20 has a fixed grip part 22 and a movable grip part 24. In other configurations not shown here, however, both grip parts 22 and 24 can also be movable. The movable grip part 24 can be movably mounted so as to be pivotable about an axis of rotation 25, as is illustrated with a double arrow 27.

The grip part 22 and the grip part 24 are equipped with a finger ring 28, 30 in each case in the exemplary embodiment such that the handle 20 can be held and actuated with two fingers of the same hand. The configuration of the handle 20 as a scissor grip assembly shown here is, however, only exemplary. In other configurations, the handle 20 can be designed for example as a rod grip assembly, which can be enclosed by a hand and actuated.

The instrument 10 also has an elongated force transmission element 32, which extends in the longitudinal direction of the shaft 12, normally in the interior of the shaft 12, from the handle 20 to the tool 14. The force transmission element 32 has, as shown in FIG. 5, a, for example, spherical head 34, which is received in a corresponding receiving portion 36 (see also FIGS. 2 and 6) on the movable grip part 24. The receiving portion 36 is designed corresponding to the shape of the head 34 in a complementary manner to the head 34, in the present exemplary embodiment, the receiving portion 36 can be correspondingly designed as a ball holder.

At the distal end, the force transmission element 32, which can also be designated as a pulling or compressing rod, is operatively connected to the tool 14. The force transmission element 32 is longitudinally movable in the direction of its longitudinal extension, wherein the longitudinal movability serves to move the tool 14. The longitudinal movability of the force transmission element 32 is illustrated in FIG. 1 with a double arrow 37. When for example the movable grip part 24 is pivoted towards the stationary grip part 22, the force transmission element 32 is moved proximally. This proximally directed longitudinal movement of the force transmission element 32 serves to move the tool in a first direction, in the present exemplary embodiment serving to open the tool 14. The reverse pivoting movement of the movable grip part 24 pushes the force transmission element 32 in the longitudinal direction distally, wherein this longitudinal movement of the force transmission element 32 serves to move the tool 14 in an opposing manner, here to close the tool 14. This type of actuation mechanism is, however, only exemplary. For example, in other configurations, the proximally directed movement of the force transmission element 32 can serve to open the tool 14 and the distally directed longitudinal movement of the force transmission element 32 serves to close the tool 14.

The handle 20 also has a housing 38 for fastening the shaft to the handle 20.

With reference to FIGS. 2 to 6, a self-locking mechanism 40 is described below, which prevents the tool 14 from moving when a force is acting on the tool 14, while the movement of the tool 14 is free when the movable grip part 24 is actuated. The self-locking mechanism 40 can be implemented in the instrument 10 in FIG. 1. In FIGS. 2 to 6, the same reference numerals as in FIG. 1 are therefore used for elements or parts corresponding to parts or elements of the instrument 10 in FIG. 1. FIGS. 2 to 6 show only the handle 20, wherein the movable grip part 24 is shown only in sections. The shaft 12 and the tool 14 are omitted for reasons of clarity. The force transmission element 32 is shown in FIG. 5 in its proximal region.

The self-locking mechanism 40 arranged on the handle 20 has a spring assembly 42. The spring assembly 42 has at least one leg spring 44. In the present exemplary embodiment, the spring assembly 42 has in total four leg springs 44a, 44b, 44c and 44d. The leg springs 44a, 44b, 44c and 44d can be the same as one another. The individual leg springs 44a, 44b, 44c and 44d are also designated below collectively as leg spring 44.

The leg spring 44, which can also be designated as a torsion spring, is for example formed of spring wire. The leg spring 44 has at least one winding 46 and two legs 48, 50. 'At least one winding' should be understood as the leg spring extending in the wound region by at least 360°. The leg spring can also have a plurality of windings 46. The legs 48 and 50 of the leg spring 44 project towards the same side from the at least one winding 46.

The spring assembly 42 also has a pin 52, in the exemplary embodiment shown, the spring assembly 42 has two pins 52a, 52b which are also designated collectively below as pin 52. The leg springs 44a and 44b sit on the pin 52a and the leg springs 44c and 44d sit on the pin 52b. As can be seen in FIG. 2 in connection with FIG. 6, two of the leg springs, and namely the leg springs 44a, 44b, on the one hand, and the leg springs 44c and 44d, on the other hand, are arranged in pairs on both sides of a longitudinal axis 80 of the shaft 12.

The at least one winding 46 of the leg spring 44 extends about the pin 52. The winding 46 of the leg spring 44 can thereby be wrapped tightly around the pin 52 such that the leg spring 44 in the rest state, i.e. when a force is not applied to the legs 48, 50, cannot rotate relative to the pin 52 due to a frictional engagement. The leg spring 44 could, however, also only be wrapped so tightly around the pin 52 that the leg spring 44 in the rest state can rotate relative to the pin.

The pin 52 is arranged in a rotationally-fixed manner on the handle 20. The pin 52 can be arranged, as shown in the present exemplary embodiment, such that it aligns with the axis of rotation 25. The pin 52 can have a projection 53, via which the pin 52 is fixed on the immovable grip part 22 in a rotationally-fixed manner on an articulation point 57, on which the movable grip part 24 is movably mounted. The projection 53 can be guided through an opening 54 in a section 56 of the movable grip part 24. The projection 53 can serve as a shaft for the movable grip part 24.

The receiving portion 36 for fixing the proximal end of the force transmission element 32 has blocks 58a and 58b, which are fixedly, for example integrally, connected to the receiving portion 36. The blocks 58a and 58b are also designated below collectively as block 58. The leg 50 of the leg spring 44 is fixed on the block 58 by means of a fastening element 60. The fastening element 60 can have a shim 62 and one or a plurality of screws 64, which are screwed into threaded bores 66 on the block 58. The leg 50 is accordingly clamped between the shim 62 and the block 58. For the leg 48, a fastening element 67 is provided with a shim 68 and one or a plurality of screws 70 in order to fix the leg 48, at the side of the block 58 opposite the leg 50, to said block. In this manner, the legs 48, 50 are fixedly connected to the receiving portion 36 via the block 58.

As can be seen for example in FIG. 4, the legs 48 and 50 of the leg spring 44 are arranged axially behind one another viewed in the longitudinal direction of the shaft and spaced axially apart from one another. In the exemplary embodiment shown, the legs 48 and 50 run parallel to one another.

The self-locking mechanism 40 also has a driver 72, wherein, in the present exemplary embodiment, two drivers 72a and 72b are present, which are also designated hereafter collectively as driver 72.

The driver 72 is arranged on the movable grip part 24 excentrically to the axis of rotation 25 of the movable grip part 24. When the movable grip part 24 is pivoted, the driver 72 is also moved. In the present exemplary embodiment, the movable grip part 24 has in the gable section 56 a bore 74 for fastening the driver 72. The driver 72 is arranged between the legs 48 and 50 of the leg spring 44, as can be seen in FIG. 4.

The receiving portion 36 with the block 58 is fastened in a rotationally-movable manner on the movable grip part 24 and, to this end, has an orifice 75. The receiving portion 36 is for example fixedly connected to the movable grip part 24 via a projection 73 of the driver 72, which, through a bore 74 on the section 56, engages into a bore 75 on the receiving portion 36. When the movable grip part 24 is pivoted, the receiving portion 36 is moved and thus the driver 72 along with the movable grip part 24, and namely about the axis of rotation 25. The pin 52, in contrast, is immovable when the movable grip part 24 is pivoted.

End plates 86 are fastened at the laterally outer ends of the pins 52a, 52b and together with a tab 90 passing through the fixed grip part 22 through a bore 88, form an anti-torsion mechanism for the leg spring 44.

The functioning of the self-locking mechanism 40 will be described below.

When the movable grip part 24 is actuated, depending on the direction of the actuation of the movable grip part 24, a force acts on the leg 48 or on the leg 50, said force reducing the friction between the winding 46 and the pin 52 such that the leg spring 44 can be rotated about the pin 52. This is implemented in the exemplary embodiment such that, when the movable grip part 24 is moved in the direction of an arrow 92 in FIG. 4, the driver 72 presses proximally with a force (arrow 96) on the leg 48 and, when the movable grip part 24 is moved in the direction of an arrow 94, the driver presses the leg 50 distally (arrow 98). In both cases, the actuation of the grip part 24 causes the winding 46 to enlarge in diameter, even if only slightly, whereby the friction between the winding 46 and the pin 52 is reduced or even completely removed, whereby the leg spring 44 can be rotated on the pin 52. The actuation of the movable grip part 24 is also converted into a longitudinal movement of the force transmission element 32 distally or proximally, depending on the direction of actuation of the movable grip part 24. The longitudinal movement of the force transmission element 32 causes a movement of the tool 14 at the distal end of the shaft 12.

If, in contrast, a force acts on the tool 14 and attempts to move the tool 14, this force is thus transmitted from the tool 14 to the force transmission element 32, and namely in its longitudinal direction, and is transmitted via the receiving portion 36 to the spring assembly 42 such that this force now does not act on the inside as described above, but rather on the outside on the legs 48 or 50 (arrows 100, 102), whereby the winding 46 wraps even more tightly around the pin 52 and the increasing frictional engagement prevents the leg spring 44 being able to rotate on the pin 52. Therefore, any movability of the tool 14 and of the force transmission element 32 is locked.

The self-locking mechanism 40 acts immediately when a force attempting to move the tool 14 occurs on the tool 14. The self-locking occurs regardless of whether a force attempting to open the tool acts on the tool 14, as is the case when an object is grasped between the jaw parts 16 and 18, or whether the force attempts to close the jaw parts 16, 18. In both cases, the frictional engagement between the winding 46 of the leg spring 44 around the pin 52 is not overcome. This rotationally-fixed connection can be removed only by actuating the movable grip part 24, by the driver 72 moving the legs 48 and 50 away from one another. Both the self-locking and the free mobility of the tool 14 (when the movable grip part 24 is actuated) act bidirectionally.

The self-locking mechanism 40 acts in particular in a continuous manner, i.e. the self-locking becoming effective does not depend on the position of the movable grip part 24 along the possible movement path of the movable grip part 24.

The self-locking mechanism 40 does not require a release mechanism, but rather automatically releases when the movable grip part 24 is actuated in one or another direction of movement (arrows 92, 94 in FIG. 4).

A medical instrument has an elongated shaft 12, a movable tool 14 at a distal end of the shaft 12, a handle 20 with a movable grip part 24 at a proximal end of the shaft 12, and a force transmission element 32 which can be moved in the longitudinal direction of the instrument and is operatively connected to the movable grip part 24 and to the tool 14 such that an actuation of the movable grip part 24 is converted into a movement of the tool 14. The instrument 1 has a spring assembly 42 that is arranged on the handle 20 and has at least one leg spring 44, which has at least one winding 46 and two legs 48, 50, and a pin 52, wherein the at least one winding 46 extends about the pin 52. When the movable grip part 24 is actuated, a force is applied to at least one of the legs 48, 50 of the leg spring 44, said force reducing the friction between the winding 46 and the pin 52 such that the leg spring 44 can be rotated about the pin 52 and the force transmission element 32 and the tool 14 can be moved. When a force is transmitted from the tool 14 to the force transmission element 32 in the longitudinal direction thereof, the leg spring 44 cannot be rotated about the pin 52 such that the force transmission element 32 and the tool 14 cannot be moved. It is understood that the features mentioned and explained above can be used not only in the respectively indicated combination, but also in other combinations or alone without departing from the scope of the present invention.

What is claimed is:

1. A medical instrument, having an elongated shaft, a movable tool at a distal end of the shaft, a handle with a movable grip part at a proximal end of the shaft, and a force transmission element which can be moved in the longitudinal direction of the instrument and is operatively connected to the movable grip part and to the tool such that an actuation of the movable grip part is converted into a movement of the tool, and having a spring assembly that is arranged on the handle and has at least one leg spring, which has at least one winding and two legs, and a pin, wherein the at least one winding extends about the pin, wherein the at least one winding of the at least one leg spring is tightly wrapped around the pin such that the at least one leg spring in the rest state cannot be rotated about the pin due to friction, wherein when the movable grip part is actuated, a force is applied to at least one of the legs of the at least one leg spring, said force reducing the friction between the at least one winding and the pin such that the at least one leg spring can be rotated about the pin and the force transmission element and the tool can be moved, whereas when a force is transmitted from the tool to the force transmission element in the longitudinal direction thereof, the at least one leg spring cannot be rotated about the pin such that the force transmission element and the tool cannot be moved.

2. The instrument according to claim 1, wherein upon actuation of the movable grip part, a force is applied to each one of the legs of the at least one leg spring, said force reducing the friction between the at least one winding and the pin.

3. The instrument according to claim 1, wherein the movable grip part is pivotable about an axis of rotation and wherein the pin aligns with the axis of rotation.

4. The instrument according to claim 1, wherein the movable grip part has a driver, which, when the movable grip part is actuated, exerts the force on at least one of the legs of the at least one leg spring in order to reduce the friction between the at least one winding and the pin.

5. The instrument according to claim 4, wherein the legs of the at least one leg spring project from the at least one winding towards the same side and the driver is arranged between the legs of the at least one leg spring.

6. The instrument according to claim 1, wherein a proximal end of the force transmission element is operatively connected to the movable grip part and wherein at least one of the legs of the at least one leg spring is connected to the movable grip part.

7. The instrument according to claim 1, wherein the spring assembly has at least two leg springs, which are arranged on both sides of a longitudinal central axis of the shaft.

8. The instrument according to claim 7, wherein the spring assembly has at least four leg springs, which are arranged in pairs on both sides of the longitudinal central axis of the shaft.

9. The instrument according to claim 1, wherein the at least one leg spring has a plurality of windings.

10. A medical instrument, having an elongated shaft, a movable tool at a distal end of the shaft, a handle with a movable grip part at a proximal end of the shaft, and a force transmission element which can be moved in the longitudinal direction of the instrument and is operatively connected to the movable grip part and to the tool such that an actuation of the movable grip part is converted into a movement of the tool, and having a spring assembly that is arranged on the handle and has at least one leg spring, which has at least one winding and two legs, and a pin, wherein the at least one winding extends about the pin, wherein when the movable grip part is actuated, a force is applied to at least one of the legs of the at least one leg spring, said force reducing the friction between the at least one winding and the pin such that the at least one leg spring can be rotated about the pin and the force transmission element and the tool can be moved, whereas when a force is transmitted from the tool to the force transmission element in the longitudinal direction thereof, the at least one leg spring cannot be rotated about the pin such that the force transmission element and the tool cannot be moved, wherein the force transmitted from the tool to the force transmission element in its longitudinal direction is applied to at least one of the legs, whereby the friction between the at least one winding and the pin is increased.

11. The instrument according to claim 10, wherein upon actuation of the movable grip part, a force is applied to each one of the legs of the at least one leg spring, said force reducing the friction between the at least one winding and the pin.

12. The instrument according to claim 10, wherein the movable grip part is pivotable about an axis of rotation and wherein the pin aligns with the axis of rotation.

13. The instrument according to claim 12, wherein the movable grip part has a driver, which, when the movable grip part is actuated, exerts the force on at least one of the legs of the at least one leg spring in order to reduce the friction between the at least one winding and the pin.

14. The instrument according to claim 10, wherein a proximal end of the force transmission element is operatively connected to the movable grip part and wherein at least one of the legs of the at least one leg spring is connected to the movable grip part.

15. A medical instrument, having an elongated shaft, a movable tool at a distal end of the shaft, a handle with a movable grip part at a proximal end of the shaft, and a force transmission element which can be moved in the longitudinal direction of the instrument and is operatively connected to the movable grip part and to the tool such that an actuation of the movable grip part is converted into a movement of the tool, and having a spring assembly that is arranged on the handle and has at least one leg spring, which has at least one winding and two legs, and a pin, wherein the at least one winding extends about the pin, wherein when the movable grip part is actuated, a force is applied to at least one of the legs of the at least one leg spring, said force reducing the friction between the at least one winding and the pin such that the at least one leg spring can be rotated about the pin and the force transmission element and the tool can be moved, whereas when a force is transmitted from the tool to the force transmission element in the longitudinal direction thereof, the at least one leg spring cannot be rotated about the pin such that the force transmission element and the tool cannot be moved, wherein the longitudinal movement of the force transmission element and the movement of the tool is locked both when the force acting via the tool on the force transmission element is directed distally and when the force acting via the tool on the force transmission element is directed proximally.

16. The instrument according to claim 15, wherein upon actuation of the movable grip part, a force is applied to each one of the legs of the at least one leg spring, said force reducing the friction between the at least one winding and the pin.

17. The instrument according to claim 15, wherein the movable grip part has a driver, which, when the movable grip part is actuated, exerts the force on at least one of the legs of the at least one leg spring in order to reduce the friction between the at least one winding and the pin.

18. The instrument according to claim 15, wherein a proximal end of the force transmission element is operatively connected to the movable grip part and wherein at least one of the legs of the at least one leg spring is connected to the movable grip part.

\* \* \* \* \*